United States Patent [19]

Meriläinen et al.

[11] Patent Number: 4,633,705
[45] Date of Patent: Jan. 6, 1987

[54] QUICK RESPONSE PARAMAGNETIC ANALYZER FOR MEASUREMENT OF OXYGEN CONTENTS OF GASES

[75] Inventors: Pekka Meriläinen; Osmo Toikka, both of Helsinki, Finland

[73] Assignee: Instrumentarium Corp., Finland

[21] Appl. No.: 718,547

[22] Filed: Apr. 1, 1985

[30] Foreign Application Priority Data

May 16, 1984 [FI] Finland .................................. 841961

[51] Int. Cl.⁴ ............................................ G01N 27/76
[52] U.S. Cl. ...................................................... 73/27 A
[58] Field of Search .................. 73/27 A, 23; 324/204

[56] References Cited

U.S. PATENT DOCUMENTS 3,584,499  6/1971  Hummel .............................. 73/27 A
3,866,461  2/1975  Machytka .......................... 73/27 A

FOREIGN PATENT DOCUMENTS 831965   4/1960   United Kingdom .
897179   5/1962   United Kingdom .
956818   4/1964   United Kingdom .
1236825  5/1971   United Kingdom .
1292724 10/1972   United Kingdom .

*Primary Examiner*—Stephen A. Kreitman
*Attorney, Agent, or Firm*—Andrus, Sceales, Starke & Sawall

[57] ABSTRACT

The invention relates to paramagnetic analyzer for measurement of oxygen contents of gas mixtures. The analyzer comprises electromagnet in a closed cavity controlled with chopped DC-current, sample and reference gas conduits entering the cavity and magnet core and common exit conduit. Gases are led to magnetic field in the gap between magnet poles through holes (13) and (14) drilled into the magnet core so that pedestals (15 and 16) in the gap guide gas flows to collide to be mixed. The mixed gas flows freely out from the gap to the surrounding cavity space (1).

9 Claims, 8 Drawing Figures

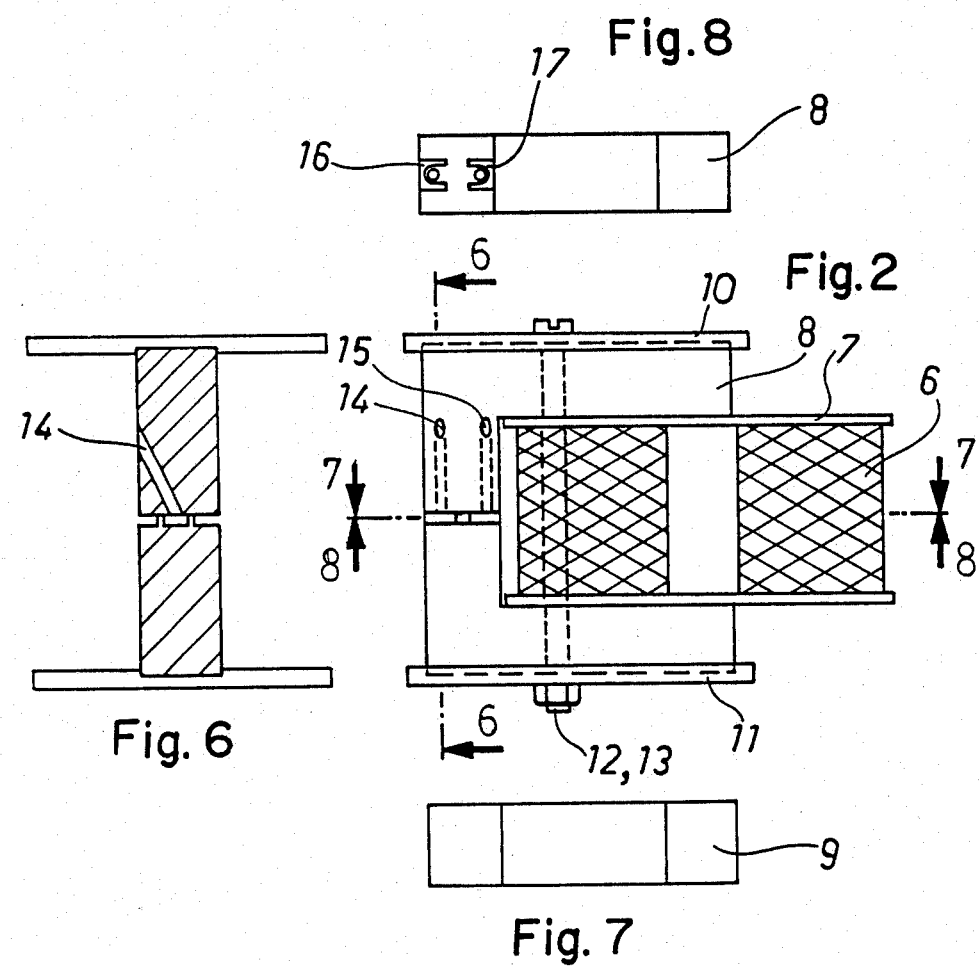

QUICK RESPONSE PARAMAGNETIC ANALYZER FOR MEASUREMENT OF OXYGEN CONTENTS OF GASES

BACKGROUND OF THE INVENTION

The strong paramagnetic property of oxygen compared to other gases has been used, as well known, for measurement of oxygen contents of gas mixtures. Especially when measuring oxygen concentration of respiration gases it would be important to reach a rapid enough (approximately 100 ms) response time to follow instantaneous concentration values. The measurement methods exploiting paramagnetism of oxygen have been based on either thermomagnetic or so called Pauling principle, which however have some drawbacks like slowness resulting from volume requirements of the measuring cell or dependence on gas flow rate.

A quick response and flow independent method based on paramagnetism of oxygen has been presented in patents DT No. 164894 and U.S. Pat. No. 3,584,499 H. Hummel. In a device according to these patents sample and reference gas are conducted to a measurement cell placed in a slot between magnet poles in such a way that the two gases will be mixed in the homogenous magnetic field and the mixed gas will be pumped out through a single conduit. Magnetic field is chopped with a proper frequency and the AC-pressure difference signal proportional to the difference of oxygen partial pressure of sample and reference gas is measured with microphone connected between gas input conduits.

Because of some drawbacks associated with construction of measurement cell, development of stable enough and noise insensitive oxygen analyser based on these patents has not been totally successful. Especially the problems seem to arise from the measurement cell, where the measurement space has been built by a separate spacer plate made of antimagnetic material and placed into the air gap of magnet. In the patent the argument for need of spacer plate is minimizing of magnetomechanical interference, but in practice sealing materials needed to ensure tightness of the construction lead to less rigid structure and in addition glueing or other bonding is difficult to make so that extra glue or bonding material will not be spread to the cell or gas conduits.

SUMMARY OF THE INVENTION

In this invention the problems are solved using a new type of construction where the measuring cell consists of a closed cavity around the magnet and the slot, where the physical effect, which the method is based on, takes place in the gradient of the magnetic field between opposite poles of the magnet is machined in a certain manner. The closed space around magnet works as a buffer volume which effectively prevents coupling of magnetomechanical disturbance to the microphone and attenuates pressure disturbances caused by the pump.

DESCRIPTION OF THE DRAWINGS

In the drawings:

FIG. 2 is a side elevation of the magnet structure;
FIG. 6 is a section taken along line 6—6 of FIG. 2;
FIG. 7 is a section taken along line 7—7 of FIG. 2;
and
FIG. 8 is a section taken along line 8—8 of FIG. 2.

DESCRIPTION OF THE ILLUSTRATED EMBODIMENT

Figure 1:
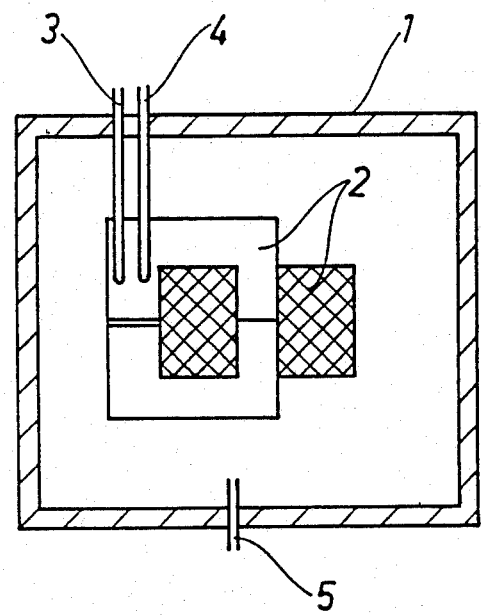
FIG. 1 is a sectional view of the measuring cell.

The measuring cell consists of an airtightly closed cavity (1), electromagnet (2), sample and reference gas conduits (3) and (4), and mixed gas outlet conduit (5). In addition, wires for magnet current and transducers measuring magnet temperature and flow density will penetrate the cavity wall.

Electromagnet consists of coil (6), bobbin (7) and magnet core halves (8) and (9) which are pressed together by means of two plates (10) and (11), and screws (12) and (13). Gases are led to the magnet gap via holes (14) and (15) drilled into the part (8). Forehead of part (8) is machined in such a way that U-shaped pedestals (16) and (17) will be formed around the gas inlet holes. The height of pedestal and the gap defined by it is typically 0.2 mm. Pedestals conduct the incoming gases to collide in such a way that they are well mixed when flowing out from the gap of magnet poles to the surrounding space. Tightness of pedestal surface against the surface of the opposite part (9) plays no critical role.

The best magnet core material is a cobalt iron mixture with a high saturation flux density of about 2.4 Teslas. This material also has a positive magnetostrictive coefficient which means that it is possible to compensate dimension changes of magnet gap due to magnetic force by proper choice of pedestal dimensions.

Force between magnet poles is $$F=(A_1B^2)/(2\mu_o)$$

where $A_1$ is gap area and B magnetic flux density. Then pressure against pedestals will be $$P=F/A_2=(A_1B^2)/(2A_2\mu_o)$$

Then pedestal strain is $$\epsilon=P/E=(A_1/2A_2)(B^2/2E\mu_o)$$

where E is elastic constant of material. On the other hand it is known that expansion by magnetostriction with saturation flux density is $\epsilon'=7\cdot10^{-5}$. By setting $\epsilon=\epsilon'$, when compression by magnetic force and expansion by magnetostriction cancel one another, we obtain $$A_1/A_2=(2E\mu_o\epsilon'/B^2)=7.32$$

This is obtained when total surface area of pedestals is 12% of magnet pole cross-section.

Figure 3:
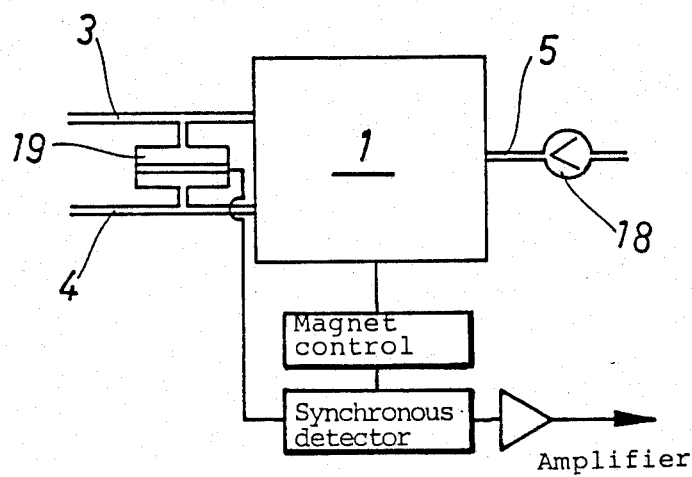
FIG. 3 is a schematic view showing the use of the measuring cell of the invention to measure the oxygen content of a gas mixture.

Measurement of oxygen contents of a gas mixture with measuring cell of this invention works as follows (see FIG. 3). Pump (18) sucks via conduit (5) sample gas led to conduit (3) and reference gas led to conduit (4) through measuring cell (1). When gases arrive from the holes of magnet to the gap between poles they pass a strong magnetic field gradient and oxygen molecules of gas will feel a force action because of their paramagnetism. Then a pressure difference will be generated in the gas between the spaces with and without magnetic field and it is proportional to the product of gas paramagnetic susceptibility and square of magnetic field. Since the mixed gases between magnet gap are in equal pressure, there will be a pressure difference between gases flowing in inlet conduits $$\Delta p = (K_s - K_r)H^2/2$$

where $K_s$ and $K_r$ are susceptibilities of sample gas and reference gas, respectively. The K of oxygen is at least 150 times as high as for example gases in respiration gases of a hospital patient, so measurement is quite specific for oxygen.

Figure 4:
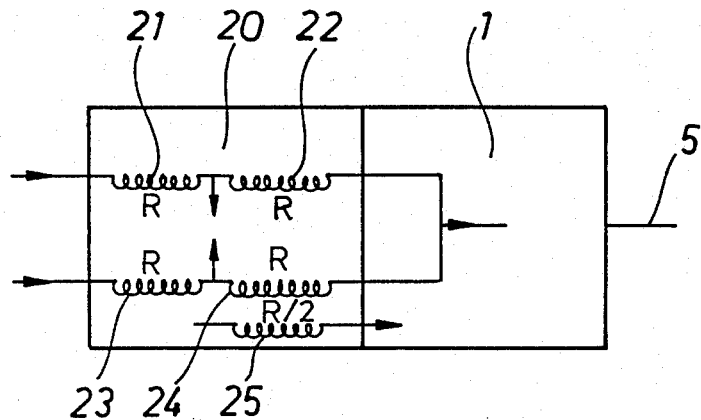
FIG. 4 is a schematic view showing the addition of a pneumatic filter circuit ahead of the measuring cell.

Magnet current is chopped typically with 100 Hz frequency and alternative pressure difference is measured by a differential microphone (19) between conduits (3) and (4). Signal is detected by a detector synchronized to magnet control and filtered and amplified as far as necessary. To ensure desired performance of the device it is, in addition, essential that sudden pressure fluctuations do not interfere with measurement. The problem is real for example when respiration gas oxygen contents of a patient coupled to respirator is measured. In this invention the problem has been solved by adding a pneumatic filter circuit in front of the measuring cell to eliminate pressure variations. The method is based on buffer volumes common to both sample and reference gas so that side flows of gases are sucked through the buffer volume. A second order pneumatic RC low pass filter realized from this principle is shown in FIG. 4. It consists of a closed cavity (20), measuring cell (1) and conduits (21-25) with high flow resistance. Purpose of conduit (25) is to carry the mixed gas out of the system bypassing the measuring cell and its flow resistance is about one half of the resistance of the other conduits.

Figure 5:
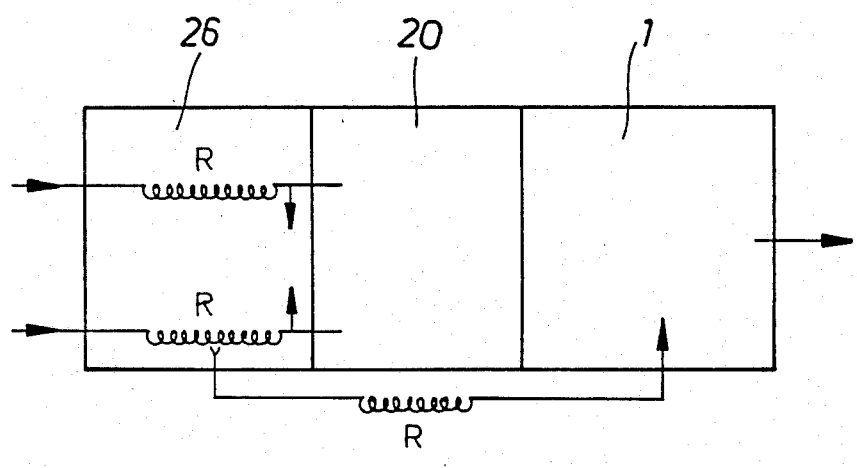
FIG. 5 is a schematic view showing the addition of a further filter stage ahead of the measuring cell.

Pressure filtering capability of the system can be increased by adding one more filter stage (26) in front of it as shown in FIG. 5. In principle even more stages could be added, but in practice finally the dominating disturbances will be those coupled directly acoustically to the microphone, which cannot be eliminated by pneumatic filtering.

Requirement for the pneumatic filtering can be estimated by assuming a sudden 10 mbar pressure change of sample gas which is possible in connection with a respirator. Pressure difference signal, equivalent to one percent of oxygen difference is about 0.3 ubar. Then one can say that pneumatic filtering must be capable of attenuating pressure change at least by a factor of 10,000 so that it would not disturb measurement too much.

We claim:

1. A measuring cell for measuring the oxygen content of a gas mixture comprising:
    a member (1) having a closed cavity therein;
    a sample gas conduit (3) extending into said cavity for supplying sample gas to said measuring cell;
    a reference gas conduit (4) extending into said cavity for supplying reference gas to said measuring cell;
    an exit conduit (5) for removing gases from said cavity;
    an electromagnet (2) positioned in said cavity, said electromagnet having a core (8, 9) with spaced opposing magnetic poles forming an air gap therebetween, said electromagnet being energizable by chopped direct current for establishing a magnetic field in said air gap, at least one of said magnetic poles having passages (13, 14) extending therethrough and opening into said air gap, said passages being connected to said gas conduits for supplying sample and reference gases to said gap; and
    pedestals (15, 16) mounted in said air gap adjacent the openings of said passages for guiding the gases for mixing in said air gap, said mixed gases being discharged into said cavity for removal via said exit conduit.

2. The measuring cell according to claim 1 wherein said pedestals are further defined as a U-shaped pedestal surrounding the opening of each of said passages in said air gap, said passage openings being located in the U-shaped bottom of said pedestals and the arms of said pedestals extending toward one another.

3. The measuring cell according to claim 1 wherein said magnetic core is formed of a material with a positive magnetostrictive coefficient and said pedestals are of such dimensions that deformation of the air gap height caused by magnetic force and magnetostriction cancel one another.

4. The measuring cell according to claim 1 further including pump means coupled to at least one of said conduits for passing gas through said measuring cell and a microphone means coupled to said gas conduits providing a signal for obtaining the oxygen content of the gas mixture.

5. The measuring cell according to claim 4 further including pneumatic filter means coupled to the gas supply side of said measuring cell for reducing pressure fluctuations in the gases supplied to measuring cell.

6. The measuring cell according to claim 5 wherein said pneumatic filter means includes gas flow resistances and buffer volumes for reducing pressure fluctuations in at least a portion of the sample and reference gases.

7. The measuring cell according to claim 1 further including pneumatic filter means coupled to the gas supply side of said measuring cell for reducing pressure fluctuations in the gases supplied to measuring cell.

8. The measuring cell according to claim 7 wherein said pneumatic filter means includes gas flow resistances and buffer volumes for reducing pressure fluctuations in at least a portion of the sample and reference gases.

9. The measuring cell according to claim 1 further defined as a cell for measuring of one of oxygen partial pressure and oxygen concentration of a gas mixture.

* * * * *